United States Patent [19]

Schaefer

[11] 4,375,967
[45] Mar. 8, 1983

[54] DENTAL COMPOSITION CONTAINING X-RAY OPAQUE MATERIAL

[75] Inventor: Roland Schaefer, Friedrichsdorf, Fed. Rep. of Germany

[73] Assignee: Kulzer & Co. GmbH, Bad Homburg von der Howe, Fed. Rep. of Germany

[21] Appl. No.: 295,700

[22] Filed: Aug. 24, 1981

[30] Foreign Application Priority Data

Oct. 21, 1980 [DE] Fed. Rep. of Germany ....... 3039664

[51] Int. Cl.$^3$ ................................................ A61K 6/08
[52] U.S. Cl. ...................................... 433/199; 106/35; 260/998.11; 433/201; 433/202; 433/218; 433/228; 523/117; 524/450
[58] Field of Search ............... 433/199, 201, 202, 228, 433/218; 423/328; 260/998.11; 106/35; 523/117; 524/450

[56] References Cited

U.S. PATENT DOCUMENTS

| | | |
|---|---|---|
| 2,882,243 | 4/1959 | Milton .................................. 423/329 |
| 3,036,980 | 5/1962 | Dunham et al. ..................... 252/430 |
| 3,036,984 | 5/1962 | O'Connor et al. ................... 252/430 |
| 3,066,112 | 1/1962 | Bowen .................................. 260/41 |
| 3,539,526 | 1/1968 | Bowen .................................. 260/41 |
| 3,721,644 | 12/1970 | Stoffey et al. .................... 260/41 A |
| 3,799,905 | 9/1971 | Holloway et al. ............. 260/37 EP |
| 3,959,212 | 6/1974 | Rockett et al. .................. 260/42.53 |
| 4,028,325 | 3/1975 | King et al. ........................ 260/42.15 |
| 4,029,632 | 6/1977 | Gross et al. ....................... 260/42.15 |
| 4,220,582 | 9/1980 | Orlowski et al. .................... 433/228 |

*Primary Examiner*—Lorenzo B. Hayes
*Attorney, Agent, or Firm*—Frishauf, Holtz, Goodman & Woodward

[57] ABSTRACT

An improved dental composition which is opaque to X-rays comprising a polymerizable matrix and inorganic filler. The inorganic filler are formed of particles of zeolitic alumino-silicate of at least one metal selected from the group consisting of calcium, strontium, barium, lanthanum, rare earth metal having an atomic number of 58-71, tantalum and hafnium. The invention also provides dental prosthetic appliances found from said dental compositions.

15 Claims, No Drawings

DENTAL COMPOSITION CONTAINING X-RAY OPAQUE MATERIAL

The present invention provides dental compositions containing materials which polymerize to form a hard composition and which also contains a filling agent which is opaque to X-rays.

BACKGROUND OF THE INVENTION

The development of synthetic dental materials by Rafael L. Bowen disclosed in U.S. Pat. No. 3,066,112 was of great importance. Bowen disclosed the use of the reaction products of glycidylacrylate and glycidylmethacrylate with bisphenols and particularly the reaction product of glycidylmethacrylate and bisphenol. A (Bis-GMA) in place of the methylmethacrylate which was used up to that time. These resins were used to form compositions which also contained quartz glass treated with a vinyl silane present as an inorganic filler.

Since that time a great number of monomers suitable as bonding agents when polymerized have been disclosed. Inorganic filling materials have also been disclosed. The art has also disclosed catalysts and catalyst systems for the polymerization of the resin components to provide improved dental materials, see for example German Disclosure documents 15 70 971; 23 12 258; 23 12 559; 24 19 887; 26 58 538; 28 56 550; German Pat. No. 23 47 591; and U.S. Pat. Nos. 3,721,644; 3,799,905; and 4,028,325.

The polymerized resin which forms the binder of the dental compositions has shrinkage characteristics and coefficient of thermal expansion characteristics which are high when compared to the corresponding characteristics of hard tooth tissues. The inclusion of inorganic fillers in the dental composition reduces the differences. The compositions which contain the inorganic fillers also have higher compressive strength.

The early synthetic dental compositions could be polished to a high luster. However the synthetics containing the fillers which were first used could not be polished to a high luster. Fillers are now known which can be polished to a high luster and therefore provide aesthetically satisfactory dental artifacts such as dental fillings and dental prosthetics as disclosed in U.S. Pat. No. 4,029,632.

The synthetic dental materials prepared by polymerizing resins are transparent to X-rays and therefore do not show up on X-ray film. Inorganic fillers may also be useful to make the composition opaque to such radiation and therefore cause the set dental composition in the tooth to become visible when exposed to X-rays. U.S. Pat. No. 3,539,526 discloses a fine-grained glass made up of $SiO_2$, $BaF_2$, $Al_2O_3$ and $B_2O_3$ as a filler for dental compositions which imparts X-ray opacity to the composition.

U.S. Pat. No. 3,959,212 discloses a similar X-ray opaque filler for dental compositions comprising a crystalline barium silicate ($Ca_2Ba(SiO_3)_3$, $BaAl_2Si_2O_8$, and $BaMgCa_2Si_2O_8$). U.S. Pat. No. 4,215,033 discloses a semi-porous filler formed from a two phase glass composed of $SiO_2$, $B_2O_3$, $Al_2O_3$ and SrO, wherein one of the phases is removed to form the porous surface.

It is an object of the present invention to provide dental compositions which when polymerized set to form dental fillings and other prosthetic dental artifacts which contain a fine grained filler and which are opaque to X-rays and which, after setting (curing) have high compressive strength and good abrasion resistance as well as the ability to polish up to form a high gloss comparable to that which may be formed on a cured synthetic which does not contain filler.

THE INVENTION

The present invention provides dental compositions containing binder components which will polymerize to form a hard and strong dental prosthetic appliance. The dental composition contains a filler which imparts X-ray opacity to the composition and which also strengthens the cured composition and also provides a cured composition which can be polished to a high gloss or luster. The fillers are aluminosilicates of at least one metal selected from the group consisting of calcium, strontium, barium, lanthanum, the rare earth metals, tantalum and hafnium which are aluminum silicate zeolites. The rare earth metals are those having atomic numbers from 58 to 71 and preferably cerium. The invention also provides prosthetic dental applicances utilizing said zeolitic aluminosilicate-containing compositions. The prosthetic dental appliances are of the type disclosed in U.S. Pat. No. 4,029,632 which is incorporated by reference.

The compositions of the present invention are also particularly advantageous when the filler material is formed from a zeolitic alumino silicates which has been treated with a silane such as a vinyl silane, e.g., γ-methacryloyloxypropyltrimethoxysilane or vinyltriethoxysilane, of the type disclosed in German Pat. No. 19 37 871. The zeolitic alumino silicates utilized as the filler in the compositions of the present invention may be produced by treating sodium zeolites (alumino silicates) by cation exchange with the metal utilized in the fillers of the present invention. The zeolitic alumino-silicates used in the present invention have particles in the range of from about 0.05 to 200 μm, and preferably about 0.1 to 100 μm.

The zeolitic alumino-silicates utilized in the present invention are admixed with the binder components which form the binder upon polymerization in an amount between about 30% and 85% by weight, and preferably in an amount between about 50% and 85% by weight.

The admixture of the zeolitic alumino-silicate filler with the mixture of monomers and other resin components provide a composition having a pasty consistency and good plasticity which is not adherent and therefore can be readily processed.

The X-ray opaque dental compositions of the present invention are suitable for the manufacture of the usual range of dental artifacts including dental fillings and dental sealings, crowns, bridges, dental prosthesis and artificial teeth.

When the compositions are utilized and set (cured) to form the radiopaque dental artifact, the product is very resistant to compression and abrasion and can be polished so that the luster matches that of dental artifacts made from cured resins which do not contain fillers. Dental artifacts were tested and compressive strengths between about 365 and 500 MPa were measured and flexural strengths between about 100 and 135 MPa were measured.

The bonding agents which when set or cured polymerize to form the binder component of the dental composition and which are sometimes are referred to herein as monomers are known materials of this type which may be used to form polymerized dental appliances. The esters of acrylic and of methacrylic acid with mono- and polyhydric alcohols are preferred, such as Bis-GMA disclosed by Bowen and the so called urethane acrylates and urethane-methacrylates *
*known from German Disclosure document 23 12 559.

The dental compositions of the present invention may be polymerized utilizing known polymerization catalysts. Consideration must be given as to whether the polymerization takes place in the mouth or in the workshop. Polymerization may be carried out at room temperature (cold polymerization), or under the application of heat or under the application of radiation using visible or ultraviolet light (photo polymerization).

A mixture of dibenzoyl peroxide and N,N-dimethyl-p-toluidine is a suitable catalyst for cold polymerization. Dibenzoyl peroxide is a suitable catalyst for heat polymerization. Photo polymerization catalysts include for example a mixture of benzil and N,N-dimethylaminoethyl-methacrylate or benzoinmethylether.

The dental compositions of the present invention are further illustrated in the following examples:

EXAMPLE 1

Zeolitic cerium alumino-silicate having a particle size of 1-2 μm is treated with γ-methacryloyloxypropyl-trimethoxysilane as disclosed in U.S. Pat. No. 4,029,632 which is incorporated by this reference.

Seventy two grams of the cerium alumino-silicate which was treated with said silane was thoroughly kneaded with a solution of 0.1 gram of dibenzyl peroxide which had been admixed in a mixture of 27.9 grams comprising 60% by weight of urethanemethacrylate which had been obtained by reacting 2,4,4-trimethyl-hexamethylenediisocyanate and hydroxyethylmethacrylate, and 40% by weight of triethyleneglycoldimethacrylate. The composition was then dyed to the desired color and a paste formed which was usable for the manufacture of artificial teeth. The composition was molded and polymerized at 95° C. at a pressure of 5 bar for twenty minutes. Test specimens which were formed were tested and determined to have a compressive strength of 505 MPa and a flexural strength of 136 MPa.

EXAMPLE 2

Zeolitic calcium alumino-silicate of a particle size of 10–40 μm was treated with the same silane as in Example 1. 72 grams of the calcium alumino-silicate treated with said silane was then thoroughly kneaded with a solution of 0.1 gram dibenzyl peroxide which was admixed in 27.9 grams of the same mixture disclosed in Example 1. Test specimens were formed by polymerization at 95° C. at a pressure of 5 bar for twenty minutes. Specimen were tested and determined to have a compressive strength of 365 MPa and a flexural strength of 100 MPa.

EXAMPLE 3

Zeolitic barium aluminosilicate having a particle size of 2–4 μm was treated with a silane as disclosed in Example 1. Seventy two grams of the silane treated barium aluminosilicate was kneaded with a solution of 0.1 grams of dibenzoyl peroxide admixed in a 27.9 gram mixture having a composition and having been formed as disclosed in Example 1 to form a species of the dental composition of the present invention in paste form which was then polymerized and tested as disclosed in Example 1. The test specimens were determined to have a compressive strength of 465 MPa and a flexural strength of 132 MPa.

The dental composition of the examples can be cured into a suitable bridge or crown shape of the type illustrated in U.S. Pat. No. 4,029,632 in a mold form at 95° C. in 20 minutes.

The aluminosilicates are also known as "aluminum silicates".

What is claimed is:

1. A dental composition which when polymerized is (i) opaque to X-ray radiation and which (ii) can be polished to a high gloss comprising a polymerizable binder which polymerizes to form a polymerized dental composition and contains fine particles of an inorganic filler which imparts X-ray opacity to said composition, said inorganic filler comprising a zeolitic alumino silicate of at least one metal selected from the group consisting of calcium, strontium, barium, lanthanum, rare earth metals having atomic numbers from 58–71, tantalum, and hafnium, said polymerizable binder is at least one binder selected from the group consisting of the esters of acrylic acid with mono- and polyhydric alcohols, urethane-acrylates, urethane-methacrylates and the reaction product of glycidyl-methacrylate and bisphenol A.

2. The composition of claim 1 containing said zeolitic alumino-silicate in an amount between 30% and 85% by weight.

3. The composition of claim 2 wherein said zeolitic alumino-silicate is in the form of particles having a size of between about 0.05 and 200 μm.

4. The composition of claim 1 wherein said zeolitic alumino-silicate has been treated with an organic silane.

5. The composition of claim 3 wherein said zeolitic alumino-silicate has been treated with an organic silane.

6. The composition of any one of claims 1, 2, 3, 4, or 5 wherein said zeolitic alumino-silicate is a cerium alumino-silicate.

7. A prosthetic dental appliance comprising a shaped body portion which is opaque to X-rays which is produced by shaping and curing the dental composition of claim 1.

8. A prosthetic dental appliance comprising a shaped body portion which is opaque to X-rays which is produced by shaping and curing the dental composition of claim 6.

9. The composition of claim 6, wherein said polymerizable binder is at least one binder selected from the group consisting of the esters of acrylic acid with mono- and polyhydric alcohols, urethane-acrylates, and urethane-methacrylates.

10. The composition of claim 6, wherein said polymerizable binder is the urethane-methacrylate obtained by reacting 2,4,4-trimethylhexamethylenediisocyanate, hydroxyethylmethacrylate, and triethyleneglycoldimethacrylate.

11. The composition of claim 6, wherein said polymerizable binder is the reaction product of glycidylmethacrylate and bisphenol A.

12. A prosthetic dental appliance comprising a shaped body portion which is opaque to X-rays which is produced by shaping and curing the dental composition of claim 9.

13. A prosthetic dental appliance comprising a shaped body portion which is opaque to X-rays which is produced by shaping and curing the dental composition of claim 10.

14. A prosthetic dental appliance comprising a shaped body portion which is opaque to X-rays which is produced by shaping and curing the dental composition of claim 11.

15. The composition of claim 10 wherein said polymerizable binder is a mixture of 60% by weight of said urethane-methacrylate and 40% by weight of said triethyleneglycoldimethacrylate.

* * * * *